United States Patent
Londot

(10) Patent No.: US 9,737,233 B2
(45) Date of Patent: Aug. 22, 2017

(54) MEDICAL DEVICE FOR USE WITH NEUROMONITORING EQUIPMENT

(76) Inventor: Ryan A. Londot, St. Joseph, MI (US)

( * ) Notice: Subject to any disclaimer, the term of this patent is extended or adjusted under 35 U.S.C. 154(b) by 948 days.

(21) Appl. No.: 12/877,366

(22) Filed: Sep. 8, 2010

(65) Prior Publication Data

US 2011/0060240 A1 Mar. 10, 2011

Related U.S. Application Data

(60) Provisional application No. 61/240,826, filed on Sep. 9, 2009.

(51) Int. Cl.
*A61B 5/053* (2006.01)
*A61B 5/00* (2006.01)
*A61B 17/70* (2006.01)
*A61B 17/86* (2006.01)

(52) U.S. Cl.
CPC ............ *A61B 5/053* (2013.01); *A61B 5/6846* (2013.01); *A61B 17/7092* (2013.01); *A61B 17/864* (2013.01); *A61B 17/866* (2013.01)

(58) Field of Classification Search
CPC ... A61B 5/053; A61B 17/864; A61B 17/7092; A61B 17/686; A61B 17/8685; A61B 17/7062; A61B 17/7071; A61B 2017/7073; A61B 17/7074; A61B 17/7032; F16B 35/041
USPC .............. 600/547, 546, 554, 301, 372, 373; 606/301, 304, 279, 275; 607/51, 52; 411/381–385, 395, 424; 200/506, 507; 324/500, 509, 522, 523, 525, 526, 537, 324/755.01
See application file for complete search history.

(56) References Cited

U.S. PATENT DOCUMENTS

| | | | |
|---|---|---|---|
| 6,778,861 B1 * | 8/2004 | Liebrecht et al. | 607/116 |
| 6,925,333 B2 * | 8/2005 | Krebs | 607/116 |
| 7,120,992 B2 * | 10/2006 | He | A61N 1/3605 600/554 |

(Continued)

OTHER PUBLICATIONS

Darden, et al. "A comparison of impedance and electromyogram measurements in detecting the presence of pedicle wall breakthrough." Spine 23.2 (1998): 256-262.*

(Continued)

*Primary Examiner* — David J McCrosky
(74) *Attorney, Agent, or Firm* — Terry M. Sanks, Esq.; Beusse Wolter Sanks & Maire, PLLC

(57) ABSTRACT

A system and method to detect fracture in a pedicle portion of a vertebra. The system includes a longitudinal member adapted for insertion into a pedicle and a sensor including first and second electrical contacts for connection to first and second portions of the longitudinal member. The longitudinal member includes a head portion having an opening extending axially within the longitudinal member. A conducting rod is positioned within the opening and is electrically coupled to the longitudinal member distal from the head portion. An insulating sleeve is interposed between the longitudinal member and the conducting rod, where the longitudinal member and the conducting rod form an electrically conductive path for connection to first and second contacts, respectively. The sensor is adapted to detect a breach in a pedicle based on a change in an electrical impulse signal between the first and second contacts.

18 Claims, 5 Drawing Sheets

(56) References Cited

U.S. PATENT DOCUMENTS

| | | | |
|---|---|---|---|
| 8,348,983 B2* | 1/2013 | Neubardt | A61B 17/8625 600/372 |
| 8,380,319 B2* | 2/2013 | Berger | 607/51 |
| 8,382,413 B2* | 2/2013 | Nguyen et al. | 411/383 |
| 2004/0243207 A1* | 12/2004 | Olson et al. | 607/116 |
| 2008/0125637 A1* | 5/2008 | Geist et al. | 600/372 |
| 2008/0221473 A1* | 9/2008 | Calancie et al. | 600/546 |
| 2010/0106198 A1* | 4/2010 | Adcox et al. | 606/301 |

OTHER PUBLICATIONS

Myers, et al. "Measurement of vertebral cortical integrity during pedicle exploration for intrapedicular fixation." Spine 20.2 (1995): 144-147.*

* cited by examiner

MEDICAL DEVICE FOR USE WITH NEUROMONITORING EQUIPMENT

This application claims priority from provisional U.S. Application No. 61/240,826 filed Sep. 9, 2009, and entitled "Medical Device for Use with Neuromonitoring Equipment."

BACKGROUND OF THE INVENTION

The present invention relates to systems and methods for spinal surgery. More particularly, the present invention relates to systems and methods for detecting fracture in vertebrae during the insertion and setting of a pedicle screw.

In the treatment of spinal conditions caused by abnormal motion of the vertebrae, it is often desirable to combine two or more vertebrae in the thoracic, lumbar, or transperitoneal portion of the spine. Spinal fusion is one such surgical procedure by which two or more vertebrae are fused together with the aid of screws through the pedicles of affected vertebrae. According to this procedure, the location for a screw opening is first identified in the pedicle of a vertebra. A pilot hole is then formed at each opening with a probe or a drill. Once the pilot holes are formed, a screw is driven into each pilot hole by a suitable instrument. This process is generally repeated for an adjacent vertebra. Metal rods are then secured to adjacent pedicle screws on corresponding sides of the vertebrae to effectively "fuse" adjacent vertebra together.

Proper placement of a pedicle screw according to this procedure is shown in FIGS. 1A-B. When a pedicle screw 10 is properly aligned within the pedicle portion 12 of the vertebra 14, the threaded portion of the screw 10 is disposed entirely within the vertebra 10. If a pedicle screw 10 is improperly aligned, however, the pedicle 12 can become breached, cracked, or otherwise compromised. Potentially, the threaded portion of the screw 10 can breach the vertebra cortex 16 and impinge adjacent nerves. As a result, various attempts have been undertaken to detect fracture in a pedicle portion of a vertebra. One method involves the application of an electric potential to the pilot hole during its formation in the pedicle. According to this method, a lead wire is placed within the pilot hole, or to the pedicle screw once it is placed, and an impulse current is applied to the lead wire. If the pedicle is breached, one or more muscle groups can contract in response to the impulse current. The contraction can be detected visually or with the aid of one or more recording electrodes. If the pedicle has not been breached, the pedicle effectively insulates the impulse current, preventing a contraction of the patient's muscle groups.

There are a number of problems with the above method. First, recording electrodes, if used, are subject to misapplication and therefore will not accurately indicate a breach in the pedicle. Second, the L1 vertebra up to and including the T6 vertebra innervate abdominal muscles whose contraction can be difficult to monitor, particularly for overweight patients. Third, there are no suitable recording sites corresponding to the T6 vertebra up to and including the T2 vertebra.

Therefore, there remains a need for a low-cost system and method for detecting fracture in a pedicle portion of a vertebra at all levels. In particular, there remains a need for an improved system and method for detecting fracture of a pedicle portion of a vertebra during application of a pedicle screw while offering greater accuracy over conventional methods of fracture detection.

SUMMARY OF THE INVENTION

The present invention provides a system and method to more accurately detect fracture in a pedicle portion of a vertebra. According to one aspect of the invention, the system includes a pedicle screw for connection to a neuromonitoring sensor having first and second leads. The pedicle screw can include a longitudinal member, a conducting rod, and an insulating sleeve. The longitudinal member can include a head portion having an opening extending axially within the longitudinal member. The conducting rod can be positioned within the opening and can be electrically coupled to the longitudinal member distal from the head portion. The insulating sleeve can be interposed between the longitudinal member and the conducting rod, where the longitudinal member and the conducting rod form an electrically conductive path for connection to first and second leads of the sensor proximate the exposed, trailing portion of the pedicle screw. The sensor can include a power supply adapted to apply an impulse signal to a first portion of the longitudinal member, and a detection circuit adapted to determine a change in a characteristic of the impulse signal when detected at a second portion of the longitudinal member. The sensor can be further adapted to provide a visual, audible, or haptic indication if the change is determined to indicate a potential breach in the pedicle portion of the vertebra.

According to another aspect of the invention, a method is provided for detecting a breach in a pedicle portion of a vertebra. The method includes forming a pilot hole in the pedicle, inserting a pedicle screw in the pilot hole, applying an impulse signal at a first portion of the pedicle screw, and detecting the impulse signal at a second portion of the pedicle screw. Applying an impulse signal can include applying a low current, low voltage impulse signal via a first lead to a first portion of an exposed portion of the pedicle screw. Detecting an impulse signal can include electrically connecting a second lead to a second portion of an exposed portion of the pedicle screw. Optionally, the first and second portions of the pedicle screw are in electrical communication with each other via a substantial portion of the exterior length of the pedicle screw. Detecting the impulse signal can further include determining a change in at least one of a voltage and a current of the impulse signal, the change corresponding to a breach in the pedicle portion of the vertebra. A breach—for example formed during pilot hole formation, pilot hole preparation, and/or pedicle screw insertion—can result in a change in one or more characteristics of the detected impulse signal, including a decrease in voltage or current, for example.

Accordingly, the present invention provides an effective system and method for detecting pedicle fracture during insertion of the pedicle screw or other device in the pedicle portion of a vertebra. The system and method of the present invention can greatly simplify pedicle integrity assessments over known methods, and can eliminate the need for the placement, calibration and monitoring of one or more recording electrodes on the patient's body. In addition, the system and method of the present invention can provide real-time or near real-time assessment of the pedicle during application of the pedicle screw, and can detect pedicle fractures at locations proximate to and distal from the vertebrae cortex.

These and other features and advantages of the present invention will become apparent from the following description of the invention, when viewed in accordance with the accompanying drawings and appended claims.

DETAILED DESCRIPTION OF THE CURRENT EMBODIMENT

The invention as contemplated and disclosed herein can greatly improve the insertion of a screw in the pedicle portion of a vertebra while detecting for degradation of a pedicle portion of a vertebra. In particular, the present invention includes an improved pedicle screw and method to more accurately monitor the integrity of the vertebra for pedicle fracture. While described in the form of a pedicle screw, the present invention can be adapted to virtually any medical device or fixation device, including a medical probe or drill for formation of a pilot hole, for example. In addition, the present invention can be readily utilized in non-medial applications where it is desirable to detect a change in the structural characteristics of an insulating material.

Figure 1A:
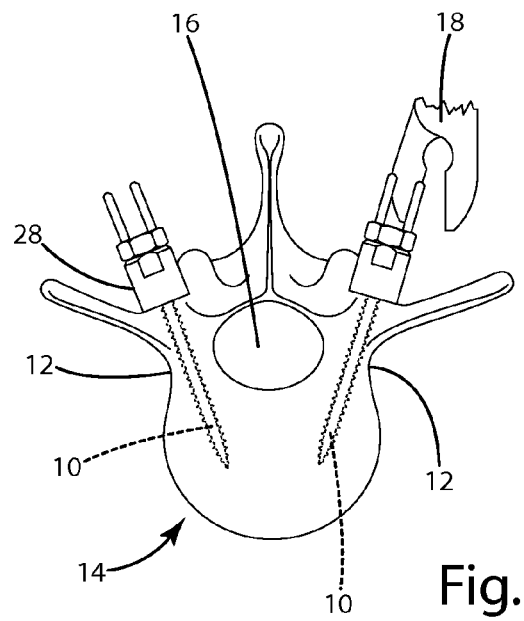
FIG. 1A is a top view of the lumbar spinal region and a prior art pedicle screw and driver.
Figure 1B:
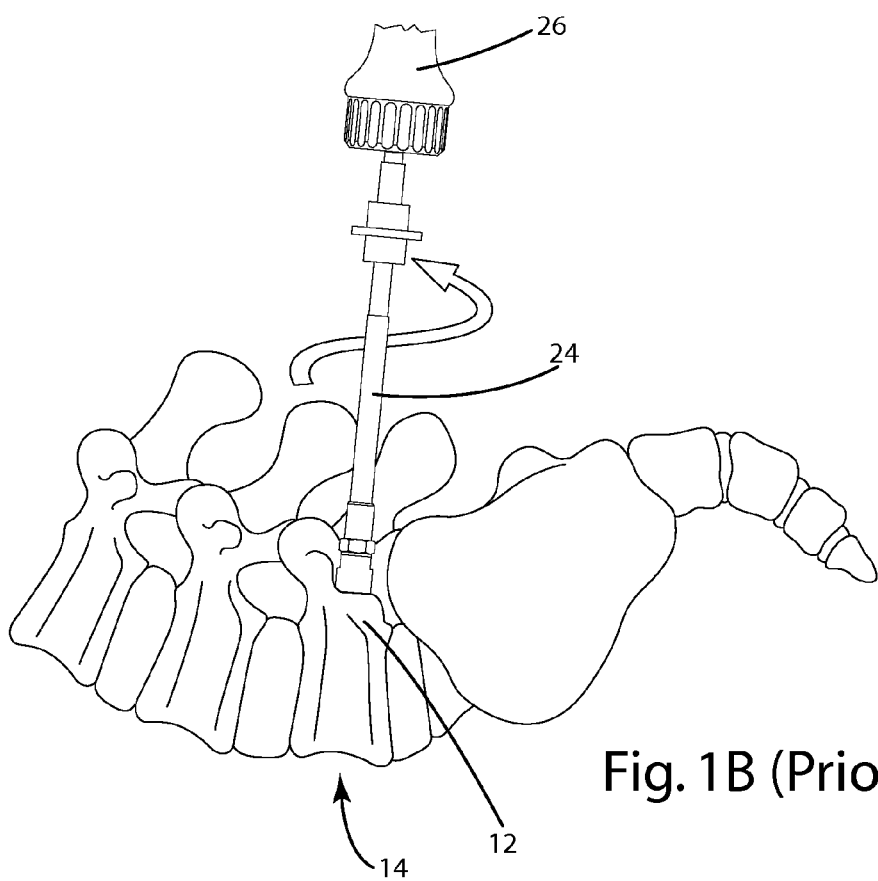
FIG. 1B is a lateral view of the lumbar spinal region and a prior art pedicle screw and driver.
Figure 2:
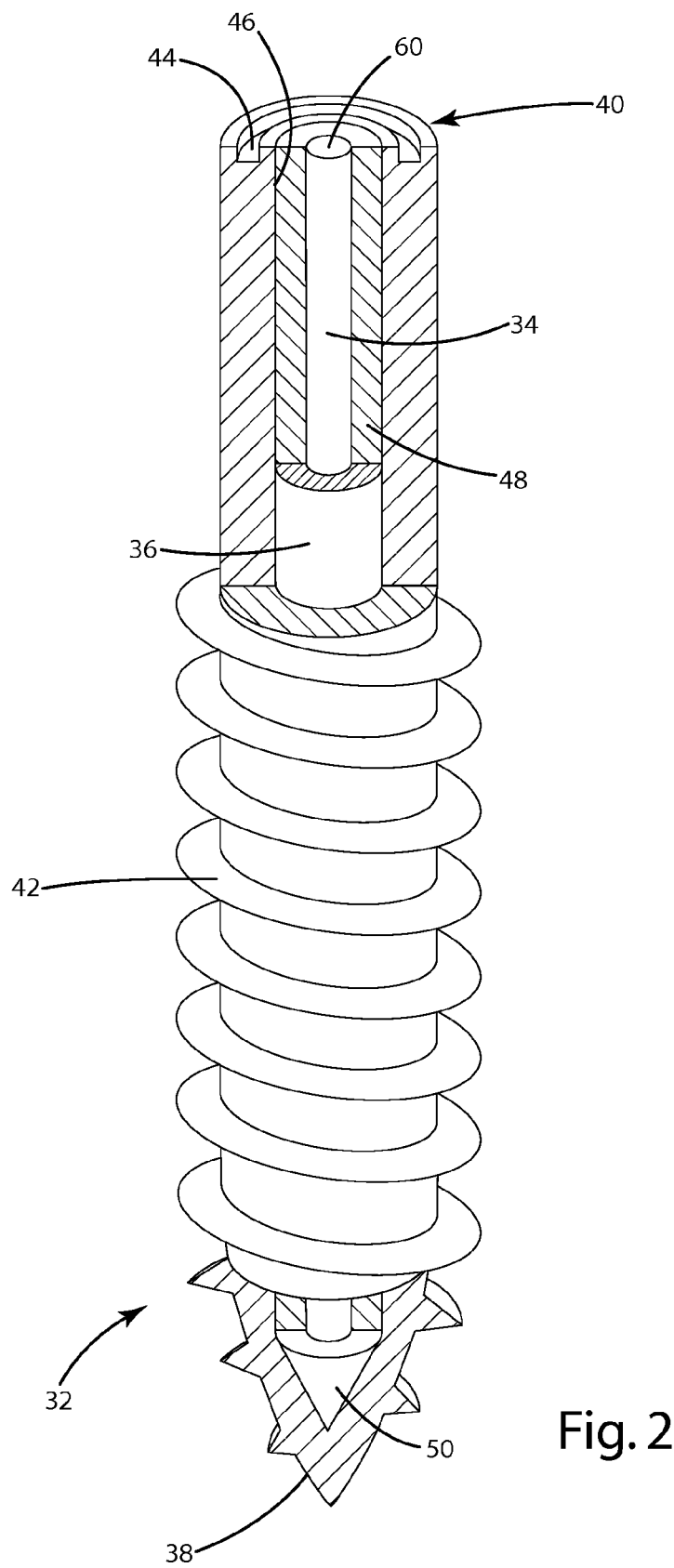
FIG. 2 is a cross-sectional view of a pedicle screw in accordance with an embodiment of the present invention.

Turning to FIG. 2, the pedicle screw 30 according to one embodiment of the present invention includes a main body 32, a center conductor 34, and an insulating sleeve 36. The main body 32 can include a tip portion 38, a head portion 40 distal from the tip portion 38, and a threaded shaft 42 therebetween. The tip 38 can be substantially conical or tapered in shape, and can be integrally formed with the threaded shaft 42 and the head portion 40. The head portion 40 can include an outer diameter equal to an outer diameter of the threaded shaft 42. Alternatively, the diameter of the head portion 40 may vary with respect to the diameter of the threaded shaft 42. The head portion 40 may further include an exposed upper end configured to couple to an insertion tool 18. For example, the exposed upper end can include a recess 44, for example an annular recess, to mateably receive a corresponding male end of an insertion tool 18, though other configurations can also be utilized. The exposed upper end of the head portion 40 can further include an opening 46 configured to receive the conductor and the insulating sleeve. The opening 46 in the exposed upper end can extend in an axial direction along a portion of the main body 32 to form a longitudinal bore 48 therein. The bore 48 can be circular in cross-section, although the bore 48 can include other cross-sections as desired. In the illustrated embodiment, the bore 48 forms an annular interior surface having a diameter less than the outer diameter of main body 32. The bore 48 is shown as extending substantially along the length of the pedicle screw main body 32, although the bore 48 may instead extend along a reduced portion of the main body 32.

As noted above, the pedicle screw 30 in one embodiment of the invention includes a conductor 34 centrally positioned within the longitudinal bore 48. The conductor 34 can be formed of a conducting material, and includes an outer diameter less than the inner diameter of the threaded shaft 42, forming an annular channel therebetween to receive the insulating sleeve. The conductor 34 can be electrically coupled to the main body 32 to allow electrical current from the conductor 34 to the pedicle screw body 32. For example, the leading end portion 50 of the conductor 34 can be bonded to the pedicle screw body 32 with an electrically conductive binder. Alternatively, the conductor 34 and the main body 32 can form a single continuous member formed of an electrically conductive material including, for example, a metal alloy. The leading end portion 50 of the conductor 34 can also include an enlarged end to releasably mate to the main body distal from the head portion 40, wherein the main body 32 and the conductor 34 form an electrically conductive path. Those skilled in the art will understand that the center conductor 34 can have an end portion 50 that is not enlarged but includes another suitable configuration to mate with the main body 32 as desired.

With further reference to FIG. 2, the insulating sleeve 36 includes a hollow tube proportioned to fit between the outer annular surface of the conductor 34 and the inner annular surface of the threaded body 32. The insulating sleeve 36 can extend substantially along the length of the longitudinal bore 48, being interposed between the center conductor 34 and the threaded body 32. The insulating sleeve 36 can be formed from any insulating material suitably adapted to resist the flow of electrical current, including a elastomeric material, a polymeric material or a ceramic material, for example. The insulating sleeve 36 can alternatively be formed of a foam or gel-like material applied to or injected within the annular channel after insertion of the center conductor within the longitudinal bore 48. Once inserted or injected within the annular channel, the insulating sleeve 36 forms an insulating barrier between the outer annular surface of the conductor 34 and the inner annular surface of the threaded body 32.

Figure 3:
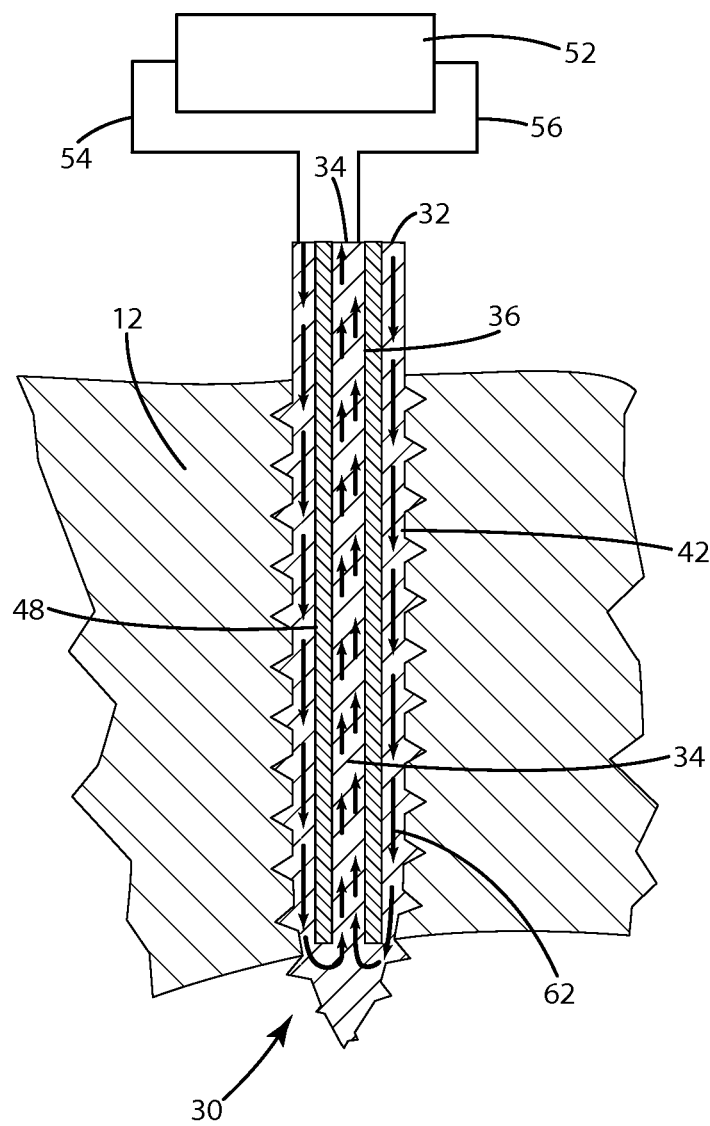
FIG. 3 is a schematic representation of the pedicle screw depicted in FIG. 2 illustrating neuromonitoring during insertion of the pedicle screw into an intact pedicle.

Turning now to FIG. 3, a pedicle screw 30 is shown as introduced into an intact pedicle 12 and electrically connected to a neuromonitoring sensor 52. In one embodiment, the neuromonitoring sensor 52 can include first and second probes 54, 56 in removable electrical contact with the pedicle screw 30. The first probe 54 can be connected to the pedicle screw main body 32 (or conductor 34), and the second probe 56 can be connected to the pedicle screw conductor 34 (or main body 32), though alternative configurations may also be utilized as desired. In this configuration, the first and second probes 54, 56 are in electrical communication with one another through the screw main body 32 and the screw conductor 34 to detect a breach in the pedicle 12. Those skilled in the art will understand that the pedicle screw 30 as illustrated in FIG. 3 can have suitable threads (not shown) to facilitate introduction of the pedicle screw 30 into the pedicle 12. In addition, the pedicle screw 30 can include a suitable head 40, for example as illustrated in FIG. 2, for connection to an insertion tool 18.

Referring again to FIG. 3, the neuromonitoring sensor 52 can include a power supply (not shown) and a detection circuit (not shown). The power supply can be adapted to deliver an impulse signal to the pedicle screw body 32 via the first probe 54. For example, the power supply can include a microcontroller-controlled switching circuit to produce a regulated neuromonitoring impulse signal to the pedicle screw body 32. The impulse signal can vary from application to application as desired. For example, the impulse signal can include a short duration pulse having constant voltage and/or a constant current. Alternatively, or in addition, the impulse signal can include a varying waveform including, for example, a series of pulses. This waveform can include a pulse width, pulse amplitude, and/or pulse duty cycle that can each be held to a single value or varied as desired.

Throughout insertion or setting of the pedicle screw 30, the detection circuit can evaluate the return impulse signal, optionally correlating the return impulse signal with the output of the power supply. In particular, the detection circuit can be adapted to distinguish the return impulse signal in situations where the pedicle 12 is not breached from situations where the pedicle 12 is breached. For example, the detection circuit can include a comparator including first and second inputs corresponding to the impulse signal and the return impulse signal, respectively. The comparator output can then be compared against a reference voltage. Where the comparator output (i.e., the difference in voltage between the impulse signal and the return impulse signal) exceeds the reference voltage, the detection circuit can indicate a potential breach in the pedicle 12. Though described above in terms of voltage, the detection circuit can also or alternatively monitor the return impulse signal for a change in other parameters, including the current, phase, duty cycle, pulse width or pulse sequence of the initial impulse signal.

Figure 4:
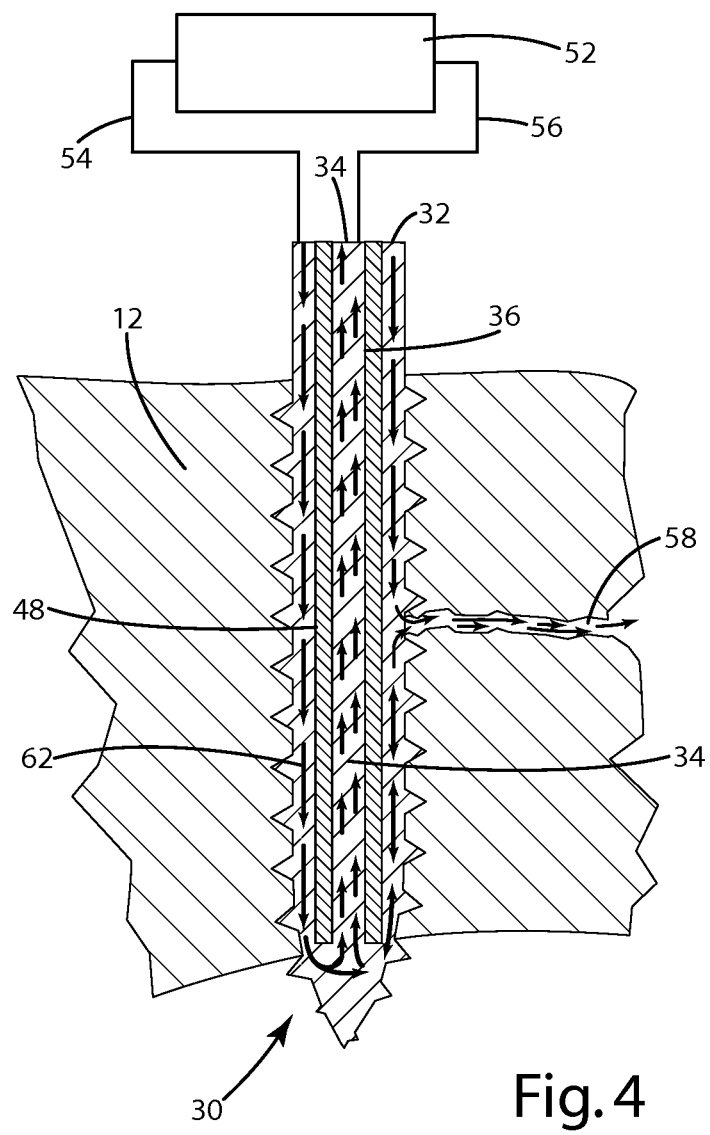
FIG. 4 is a schematic representation of the pedicle screw depicted in FIG. 2 illustrating neuromonitoring during insertion of the pedicle screw into a breached pedicle.

If the detection circuit detects a sudden or gradual change in the return impulse parameters, the neuromonitoring unit provides an alert to the operator. The alert can indicate a breach 58 in the pedicle 12, as shown in FIG. 4, where all or a portion of the impulse signal escapes to ground through the pedicle breach and into tissue surrounding the pedicle 12. The resulting alert can include a visual indication, audible indication, haptic indication, or any combination of the same. In response to this alert, the surgeon may halt insertion of the pedicle screw 30 and optionally re-align or re-set the pedicle screw 30 within the pedicle while simultaneously (or nearly simultaneously) monitoring for further breach in the pedicle 12 as described above.

Those skilled in the art will understand that the first and second probes 54, 56 as described above can be insulated except for a conductive tip at the distal end for contacting the pedicle screw body and the conductor. The neuromonitoring sensor 52 can alternatively include a single insulated probe with first and second electrical leads. For example, the probe can include first and second leads fixed in relation to one another, where the first lead is configured to contact the pedicle screw main body, optionally along a portion of the head, and the second lead is configured to contact the conductor. Alternatively, the first and second leads can form part of an instrument for driving the pedicle screw into the pilot hole. In this embodiment, the neuromonitoring sensor 52 can provide an alert in real-time as the pedicle screw 30 is set within the pilot hole.

Figure 5:
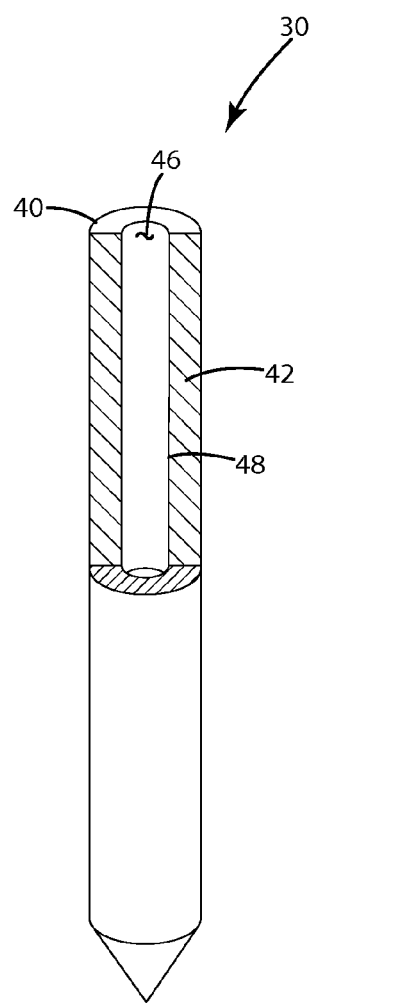
FIG. 5 is a cross-sectional view of a pedicle screw in accordance with another embodiment of the present invention.
Figure 6:
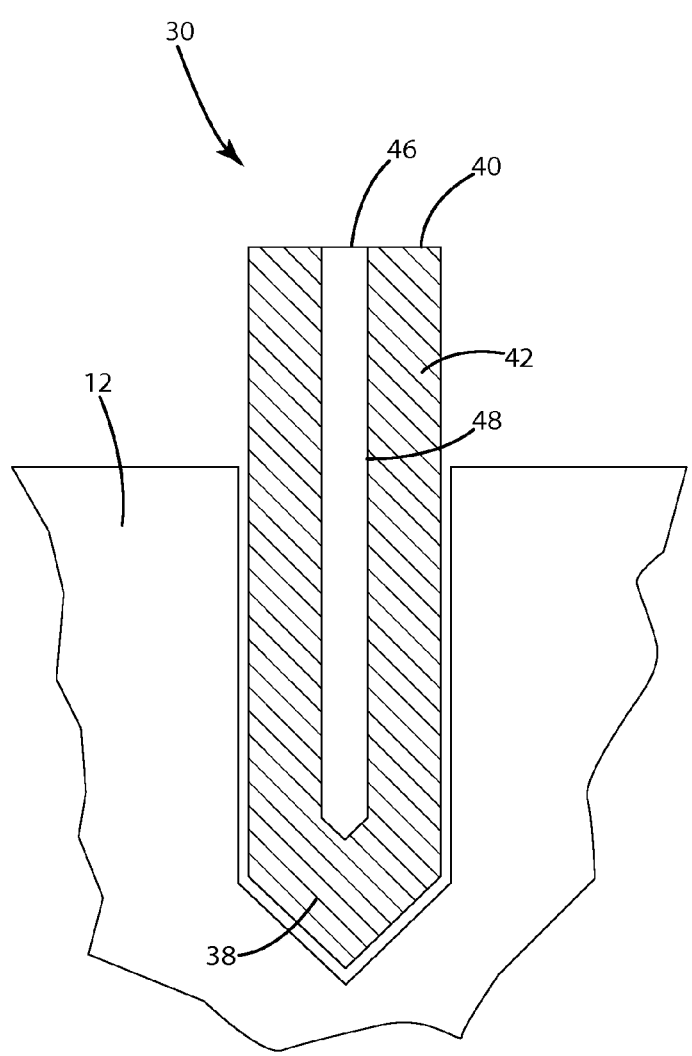
FIG. 6 is a schematic representation of the pedicle screw depicted in FIG. 5 illustrating insertion into an intact pedicle.

In another embodiment as shown in FIGS. 5-6, the pedicle screw 30 is substantially as described above in connection with FIGS. 2-4, however the pedicle screw 30 is shaped to receive an elongate probe that is removeable with respect to the pedicle screw 30. In particular, the pedicle screw includes include a tip portion 38, a head portion 40 distal from the tip portion 38, and a threaded shaft 42 therebetween. The exposed upper end of the head portion 40 can further include an opening 46 extending in an axial direction along a portion of the pedicle screw 30 to form a longitudinal bore 48 therein. The bore 48 is shown as extending substantially along the length of the pedicle screw 30, although the bore 48 may instead extend along a reduced portion of the pedicle screw.

According to the illustrated embodiment, the longitudinal bore 48 is shaped to receive an elongate probe (not shown). For example, the elongate probe can include the conductor 34 and insulating sleeve 36 of FIG. 2. In this embodiment, the elongate probe is axially removable with respect to the longitudinal bore 48, and the tip 50 of the conductor 34 extends axially beyond the insulator 36 and contacts a portion of the pedicle screw 30 proximate the tip 38. For example, when the elongate probe is positioned within the longitudinal bore 48 of the pedicle screw 30, the tip of the conductor 34 can be in electrical contact with the pedicle screw tip 38 for measuring the integrity of the pedicle using an associated neuromonitoring sensor. When the elongate probe is removed from the longitudinal bore 48 of the pedicle screw 30, the pedicle screw functions substantially as an anchoring structural member for attachment to metal rods or plates according to any suitable method, for example in the application of a spinal fusion surgical procedure.

As noted above, the elongate probe—optionally including the conductor 34 and insulating sleeve 36 of FIG. 2—can be electrically coupled to a neuromonitoring sensor. Substantially in the manner described above in connection with FIGS. 3-4, the neuromonitoring sensor can generate an impulse signal to a fist portion of the pedicle screw 30 via the elongate probe, and can evaluate the return impulse signal at a second portion of the pedicle screw 30 distal from the first portion of the pedicle screw 30. By comparing a characteristic of the return impulse signal with a characteristic of the initial impulse signal or reference signal, or by detecting a sudden change in a characteristic of the return impulse signal, the neuromonitoring sensor can rapidly identify a potential breach in the pedicle 12 adjacent the pedicle screw 30. For example, if the return impulse revealed a non-negligible change in the voltage, current, phase, duty cycle, pulse width or pulse sequence of the initial impulse signal, the neuromonitoring sensor can provide an alert to the operator substantially as described above.

An improved method of setting a pedicle screw 30 according to the present invention can include forming a pilot hole in the pedicle portion 12 of a vertebra, inserting a pedicle screw 30 in the pilot hole, applying an impulse signal at a first portion of the pedicle screw 30, and detecting the impulse signal at a second portion of the pedicle screw 30 to indicate a breach in the pedicle portion of the vertebra. The step of forming a pilot hole can include, for example, forming an incision in a patient proximate the target vertebra, identifying the pedicle portion of the target vertebra, and, using a drill bit and tap, forming a pilot hole in the target vertebra. The step of inserting the pedicle screw can be performed according to known methods, including the insertion of a threaded pedicle screw 30 with the aid of implements well known in the art. The step of applying an impulse signal at a first portion of the pedicle screw 30 can include applying a low current, low voltage impulse signal via a first probe or contact 54 to a first portion of the exposed, trailing portion 40 of the pedicle screw 30. Optionally, this first portion can include the exposed outer periphery of the pedicle screw head 40, substantially as described above in connection with FIGS. 3-4, though other locations can also be utilized. The step of detecting an impulse signal at a second portion of the pedicle screw 30 can include positioning a second probe or contact 56 to a second portion of the exposed, trailing portion of the pedicle screw. Optionally, this second portion can include the exposed trailing portion of the conductor 60, substantially as described above in connection with FIGS. 3-4, though other locations can also be utilized. In the present embodiment, the first and second portions of the pedicle screw are in electrical communication with each other along a substantial portion of the exterior length of the pedicle screw 30. That is, the pedicle screw 30 forms a conducting path 62 from the first portion to the second portion along a substantial portion of the exterior of the pedicle screw 30. The step of detecting the impulse signal can further include determining a change in at least one of a voltage and a current of the impulse signal, the change corresponding to a breach in the pedicle portion of the vertebra. When the electrical impulse signal is applied to the first portion of the pedicle screw 30, the return impulse signal can remain substantially unchanged, revealing an intact pedicle. If a breach occurs—for example during pilot hole formation/preparation, and/or pedicle screw insertion—the return impulse signal can exhibit a change in one or more characteristics, including a decrease in voltage or current. This reduction, or difference, can indicate further investigation is required.

The above description is that of current embodiments of the invention. Various alterations and changes can be made without departing from the spirit and broader aspects of the invention as defined in the appended claims, which are to be interpreted in accordance with the principles of patent law including the doctrine of equivalents. Any reference to elements in the singular, for example, using the articles "a," "an," "the," or "said," is not to be construed as limiting the element to the singular.

The invention claimed is:

1. A device for connection to a sensor including first and second contacts, the device comprising:
    an electrically-conductive longitudinal member to propagate an initial impulse signal along an exterior length, the longitudinal member including a shaft portion having a head portion at a trailing end of the longitudinal member, a closed tip at a leading end of the longitudinal member, an exterior surface, and an opening to a bore extending axially within the shaft portion from the head portion toward the closed tip, the closed tip being distal from the head portion;
    a conducting rod within the bore to propagate a return signal to the sensor, the conducting rod including a leading end that electrically contacts the closed tip of the longitudinal member and including a trailing end portion axially extending to the head portion of the longitudinal member; and
    an insulating material within the bore in the shaft portion, the insulating material being interposed between the shaft portion of the longitudinal member and the conducting rod such that the conducting rod is insulated and spaced apart from the shaft of the longitudinal member;
    wherein the longitudinal member and the conducting rod provide an electrically conductive path which extends along the longitudinal member from the head portion to the closed tip to propagate the initial impulse signal from the first contact and the electrically conductive path includes the leading end of the conducting rod to propagate the return impulse signal up to the trailing end portion of the conducting rod to the second contact, absent a pedicle fracture; and
    wherein, with a presence of the pedicle fracture, the impulse signal escapes from the longitudinal member to the pedicle fracture which causes a change in the return impulse signal propagated along the conducting rod to the second contact.

2. The device of claim 1, wherein the insulating material includes a tubular sleeve disposed about the conducting rod.

3. The device of claim 1, wherein the leading end of the conducting rod extends axially beyond the insulating material to the closed tip of the longitudinal member.

4. The device of claim 1, wherein the conducting rod and the insulating material form a removable probe for connection to at least one of the first and second contacts of the sensor, the removable probe being separate and removeable from the longitudinal member.

5. The device of claim 4, wherein the removable probe is axially inserted into the opening and bore in the longitudinal member.

6. The device of claim 1, wherein both the longitudinal member and the conducting rod form a single continuous member.

7. The device of claim 1, wherein the leading end of the conducting rod comprises an end to releasably mate to the closed tip.

8. The device of claim 1, wherein the conducting rod being bonded to the closed tip by an electrically conductive binder.

9. The device of claim 6, wherein the insulating material includes a tubular sleeve disposed about the conducting rod.

10. A system, comprising:
    a sensor having first and second contacts, the sensor to produce an initial impulse signal to the first contact and receive an expected return impulse signal at the second contact, the expected return impulse signal exhibiting a characteristic of the initial impulse signal;
    a pedicle screw comprising:
        an electrically-conductive longitudinal member to propagate the initial impulse signal along an exterior length, the longitudinal member including a shaft portion having a head portion at a trailing end of the longitudinal member, a closed tip at a leading end of the longitudinal member, an exterior surface, and an opening to a bore extending axially within the shaft portion from the head portion toward the closed tip, the closed tip being distal from the head portion;
        a conducting rod within the bore to propagate the expected return impulse signal to the sensor, the conducting rod including a leading end that electrically contacts the closed tip of the longitudinal member and including a trailing end portion axially extending to the head portion of the longitudinal member; and
        an insulating material within the bore in the shaft portion, the insulating material being interposed between the shaft portion of the longitudinal member and the conducting rod such that the conducting rod is insulated and spaced apart from the shaft of the longitudinal member;
    wherein the longitudinal member and the conducting rod provide an electrically conductive path which extends along the longitudinal member from the head portion to the closed tip to propagate the initial impulse signal from the first contact and the electrically conductive path includes the leading end of the conducting rod to propagate the expected return impulse signal up to the trailing end portion of the conducting rod to the second contact, absent a pedicle fracture; and wherein, the impulse signal escapes from the longitudinal member to the pedicle fracture, when the pedicle fracture Is present, which causes a change in the expected return impulse signal propagated along the conducting rod to the second contact.

11. The system of claim 10, wherein the sensor detects a change in electric potential between the first and second electrical contacts.

12. The system of claim 10, wherein the sensor detects a change in current between the first and second electrical contacts.

13. The system of claim 10, wherein the sensor includes: a power supply electrically connected to the first contact and adapted to generate the initial impulse signal; and a detection circuit electrically connected to the second contact and adapted to determine the change in the characteristic of the return impulse signal.

14. The system of claim 10, wherein both the longitudinal member and the conducting rod form a single continuous member.

15. The system of claim 14, wherein the insulating material includes a tubular sleeve disposed about the conducting rod.

16. The system of claim 10, wherein the conducting rod being bonded to the closed tip by an electrically conductive binder.

17. A method for detecting a pedicle fracture in a pedicle of a vertebra by a sensor having a first contact and a second contact, the method comprising:

forming a pilot hole in the pedicle of the vertebra;
providing a pedicle screw including:
an electrically-conductive longitudinal member to propagate an initial impulse signal along an exterior length, the longitudinal member including a shaft portion having a head portion at a trailing end of the longitudinal member, a closed tip at a leading end of the longitudinal member, an exterior surface, and an opening to a bore extending axially within the shaft portion from the head portion toward the closed tip, the closed tip being distal from the head portion;

a conducting rod within the bore to propagate an expected return impulse signal to the sensor, the conducting rod including a leading end that electrically contacts the closed tip of the longitudinal member and including a trailing end portion axially extending to the head portion of the longitudinal member; and an insulating material within the bore in the shaft portion, the insulating material being interposed between the shaft portion of the longitudinal member and the conducting rod such that the conducting rod is insulated and spaced apart from the shaft of the longitudinal member;

inserting the pedicle screw in the pilot hole;
applying, by the sensor, the initial impulse signal to the pedicle screw;
detecting, by the sensor, the expected return impulse signal from the conducting rod; and
determining, based on a comparison of the initial impulse signal and the detected expected return impulse signal, presence or absence of a pedicle fracture;
wherein the longitudinal member and the conducting rod provide an electrically conductive path which extends along the longitudinal member from the head portion to the closed tip to propagate the initial impulse signal from the first contact and the electrically conductive path includes the leading end of the conducting rod to propagate the expected return impulse signal up to the trailing end portion of the conducting rod to the second contact, in the absence of the pedicle fracture; and
wherein, in the presence of the pedicle fracture, the impulse signal escapes from the longitudinal member to the pedicle fracture which causes a change in the expected return impulse signal propagated along the conducting rod to the second contact.

18. The method according to claim 17, wherein the insulating material within the longitudinal bore is disposed about the circumference of the conducting rod.

* * * * *